(12) United States Patent
Wang

(10) Patent No.: US 10,202,439 B2
(45) Date of Patent: Feb. 12, 2019

(54) BIOLOGICAL THERAPEUTICS FOR INFECTION-RELATING DISORDERS OR CONDITIONS

(71) Applicant: Huiru Wang, Willowbrook, IL (US)

(72) Inventor: Huiru Wang, Willowbrook, IL (US)

(73) Assignee: B&H BIOTECHNOLOGIES, LLC, Willowbrook, IL (US)

( * ) Notice: Subject to any disclaimer, the term of this patent is extended or adjusted under 35 U.S.C. 154(b) by 0 days.

(21) Appl. No.: 14/775,984

(22) PCT Filed: Mar. 13, 2014

(86) PCT No.: PCT/US2014/025926
§ 371 (c)(1),
(2) Date: Sep. 14, 2015

(87) PCT Pub. No.: WO2014/151526
PCT Pub. Date: Sep. 25, 2014

(65) Prior Publication Data
US 2016/0024186 A1    Jan. 28, 2016

Related U.S. Application Data

(60) Provisional application No. 61/792,888, filed on Mar. 15, 2013.

(51) Int. Cl.
*A61K 35/16* (2015.01)
*A61K 39/12* (2006.01)
*A61K 39/145* (2006.01)
*A61K 39/235* (2006.01)
*A61K 39/29* (2006.01)
*A61K 47/26* (2006.01)
*C07K 16/10* (2006.01)
*A61K 39/42* (2006.01)
*A61K 39/15* (2006.01)
*C07K 16/08* (2006.01)
*A61K 39/00* (2006.01)

(52) U.S. Cl.
CPC .......... *C07K 16/1018* (2013.01); *A61K 35/16* (2013.01); *A61K 39/12* (2013.01); *A61K 39/145* (2013.01); *A61K 39/15* (2013.01); *A61K 39/235* (2013.01); *A61K 39/29* (2013.01); *A61K 39/292* (2013.01); *A61K 39/42* (2013.01); *A61K 47/26* (2013.01); *C07K 16/081* (2013.01); *C07K 16/082* (2013.01); *C07K 16/10* (2013.01); *C07K 16/109* (2013.01); *C07K 16/1027* (2013.01); *A61K 2039/545* (2013.01); *C07K 2317/21* (2013.01)

(58) Field of Classification Search
None
See application file for complete search history.

(56) References Cited

U.S. PATENT DOCUMENTS

2007/0253982 A1   3/2007   Song
2011/0263483 A1   5/2011   Li
2012/0027771 A1   3/2012   Cantor

FOREIGN PATENT DOCUMENTS

WO        2011005793        1/2011

OTHER PUBLICATIONS

Fluzone product sheet, Sanofi pasteur, 2009.*
Matrosovich et al., Natural and synthetic sialic acid-containing inhibitors of influenza virus receptor binding, 2003, Rev. Med. Virol., vol. 13, pp. 85-97.*
Rudrawar et al., Novel sialic acid derivatives lock open the 150-loop of an influenza A virus group-1 sialidase, 2010, Nature Communications, pp. 1-7.*
Yang, B. et al (2015) Neonatal *Streptococcus pneumoniae* Infection May Aggravate Adulthood Allergic Airways Disease in Association with IL-17A. PLoS ONE 10(3), pp. 1-12.

* cited by examiner

*Primary Examiner* — Benjamin P Blumel
(74) *Attorney, Agent, or Firm* — McDonnell Boehnen Hulbert & Berghoff LLP

(57) ABSTRACT

The present invention discloses products and the methods of uses of the products for preventing and treating infectious diseases and the disorders or conditions inducible by harmful antibodies. The harmful antibodies are induced during infection, or vaccination, or use of therapeutic antibodies. The products of the present disclosure comprise immunoglobulin products, serum or plasma, specific antibodies to viral pathogens.

15 Claims, 1 Drawing Sheet

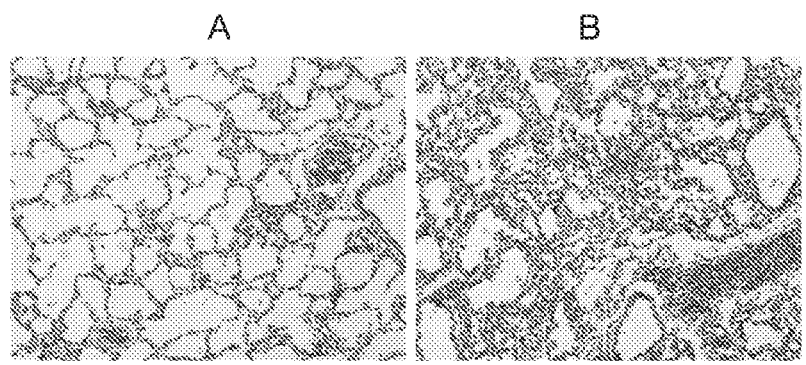

BIOLOGICAL THERAPEUTICS FOR INFECTION-RELATING DISORDERS OR CONDITIONS

CLAIM OF PRIORITY

This application claims priority to U.S. Provisional Patent Application Ser. No. 61/792,888, filed Mar. 15, 2013, entitled "Biological therapeutics for infection-relating disorders or conditions", the entire specification and disclosure of which is herein incorporated by reference.

FIELD OF INVENTION

The present disclosure relates generally to the fields of medicine and epidemiology, and in particular, to one or more products and methods for treating or preventing infections caused by viral pathogens, diseases and conditions caused by harmful antibodies which are inducible by infectious pathogens, vaccines and therapeutic antibodies.

BACKGROUND OF THE INVENTION

An infectious disease is a clinically evident disease of humans or animals. Information collected by the World Health Organization (WHO) on global deaths shows that worldwide mortality due to infectious diseases is as high as 25.9% of all deaths, or 14.7 million deaths in 2002 (WHO World Health Report 2002). The current numbers are even higher. Influenza infections especially an influenza pandemic threats people's health and economy globally. There is a big concern on a possible influenza pandemic causing by highly pathogenic H5N1 (avian or bird) influenza virus which will cause much more deaths than the 2009 swine influenza pandemic (WHO). Currently, there are no effective medicines for the treatment of a serious condition of an influenza infection especially a serious condition after 48 hours of an influenza infection.

Vaccines are the most effective approach to prevent infectious diseases. However, vaccines are not perfect as they may cause serious adverse reactions even death. For example, the swine influenza vaccine in 1976 might be related to about 500 cases of Guillain-Barré syndrome (GBS) and 25 deaths that the vaccine had to be called off (US CDC, VAERS). The 2009 monovalent H1N1 (swine) influenza vaccine might have induced 636 serious health events, including 103 cases of GBS and 51 deaths in the United States (US CDC, VAERS). Thus far, there is no direct proof between influenza vaccines and the serious side effects. Neither, there are not any medicines for preventing and treating the serious adverse reactions of influenza vaccines or other vaccines due to the unclear pathogenic mechanisms.

Every year an estimated 2.64 million babies die at 28 weeks' gestation or more (still birth) (Flenady, V., et al. Major risk factors for stillbirth in high-income countries: a systematic review and meta-analysis. Lancet, Apr. 16, 2011; 377:1331-1340), and 4 million babies die in the first 4 weeks of life (the neonatal death)(Lawn J E, Cousens S, Zupan J. 4 million Neonatal deaths: When? Where? Why? Lancet, 2005 Mar. 5-11; 365(9462):891-900). One potential risk factor may be related to infections. Nevertheless, how an infection induces fetal or neonatal deaths is unclear.

We have developed viral free animal models by injecting various anti-pathogen antibodies into chicken embryos or pregnant mice. The results of the experiments with those animal models indicated that some of anti-pathogen antibodies induced during an infection (e.g. an influenza infection) or by a vaccine (e.g. an influenza vaccine) can be harmful and cause serious conditions such as GBS even death. Therapeutic products for preventing and treating the disorders caused by such toxic antibodies were tested using the animal models.

SUMMARY OF THE INVENTION

The present invention discloses products and the methods of uses of the products for preventing and treating infectious diseases and the disorders or conditions inducible by harmful antibodies. The harmful antibodies are induced during infection, or vaccination, or use of therapeutic antibodies. The products of the present disclosure comprise immunoglobulin products, serum or plasma, specific antibodies to viral pathogens.

DETAILED DESCRIPTION OF THE PREFERRED EMBODIMENT(S)

While the present disclosure is susceptible of embodiment in many different forms, there will be described herein in detail, preferred and alternate embodiments of the present disclosure. It should be understood however, that the present disclosure is to be considered an exemplification of the principles of the invention and is not intended to limit the spirit and scope of the invention and/or claims of the embodiments illustrated.

Dualistic Roles of Antibodies

Based on the traditional concept, the antibodies induced by an infectious pathogen or by a vaccine are protective to a host because they can neutralize the pathogen and prevent or treat the infectious disease. However, the roles of such antibodies can be dualistic. Some of the antibodies can cross react to certain cells, tissues or organs of a host, triggers certain harmful reactions such as antibody-dependent cytotoxicity or defects in signal transduction pathways, and cause damages or disorders of the tissues and organs. For example, anti-viral antibodies can bind to host tissues and organs, irratate and cause disorders of the tissues and organs (e.g. autoimmune diseases as described in PCT/US2007/018258 and PCT/US2009/039810).

It is known that in an acute viral infection or a vaccination, antibodies against a pathogen (e.g. a virus) or a vaccine are induced and elevated one week after infection or vaccination and reach peak levels at two weeks after the infection or the vaccination. Some of such antibodies can bind to certain types of host cells or tissues or organs. This process can be pathogenic and cause severe diseases or conditions even death. For example, anti-rotavirus antibodies bind to the proliferating goblet cells during a rotavirus infection (PCT/US2009/039810 and US20110085981). Injection of high dose of the anti-rotavirus antibodies to pregnant mice induced deaths and bile duct epithelium proliferation (inflammation) of mouse pups born to the dames (PCT/US2009/039810, US20110085981). Further, administration of high dose of the anti-rotavirus antibodies to mouse pups before or after rotavirus infection caused deaths or severer infection of mouse pups as described in PCT/US2009/039810 and US20110085981.

In the present disclosure, the term "harmful antibodies" refers to any antibodies capable of causing pathogenic reactions and damages or disorders of the cells, tissues and organs of a host. The harmful antibodies can be induced during an infection (e.g. an influenza infection) or a vaccination (e.g. an influenza vaccination), or passively introduced (e.g. a therapeutic antibody). The diseases or conditions caused by harmful antibodies of the present disclosure include but not limited to infectious diseases, serious adverse reactions of vaccines or therapeutic antibodies, infection-relating autoimmune diseases, allergies, and inflammation, infection-relating tumors, and any other disorders (known or unknown) inducible by harmful antibodies.

Animal Models for Pathogenic Study and Evaluating the Safety of Vaccines and Antibodies One embodiment of the present invention discloses the experimental models by injecting anti-pathogen antibodies into chicken embryos or pregnant mice or newborn mouse pups. One aspect of the present invention is to disclose the experimental model which is developed by injecting human anti-influenza immune sera or other anti-pathogen antibodies into chicken embryos and observing the healthy status of the newborn chicks as described in exemplification. The human immune sera were from patients either with natural influenza infection or with influenza vaccination, or human immune sera from other infectious diseases. As described in exemplification, injection of the human anti-influenza viral sera into chicken embryo at day 16 (E16) and E19 induced the leg disability of newborn chicks which is similar to the Guillain-Barre syndrome (GBS) in humans. The frequencies of GBS-like conditions induced by the anti-influenza viral antibodies are listed in Table 1. The results with this animal model indicated that the antibodies induced by the 2009H1N1 (swine) virus is at the highest risk for inducing GBS (42.5%), followed by the antibodies induced by the B influenza virus (32.5%), the avian H5N1 virus (27.5%), the seasonal H1N1 virus (17.5%) and the H3N2 virus (15.0%). Further, injection of human anti-influenza viral sera induced fetal and neonatal deaths. The death rates are listed in Table 2. The results with this animal model indicated that the antibodies induced by the B influenza virus is at the highest risk for inducing fetal and neonatal deaths (65.0%), followed by the antibodies induced by the avian H5N1 virus (57.5%), 2009H1N1 (swine) virus (52.5%), the H3N2 virus (37.5%) and the seasonal H1N1 virus (15.0%). As a control, the anti-respiratory syncytial viruses (RSV) serum did not cause significant GBS-like condition nor deaths (Tables 1-2).

The experimental models can be used but not limited for the pathogenic study of infectious diseases, autoimmune diseases such as Guillain-Barre syndrome (GBS) or GBS-like condition, infection-relating fetal and neonatal deaths, adverse reactions of influenza vaccines and other vaccines or therapeutic antibodies; for screening drugs for prevention and treatment of the disorders or conditions caused by harmful antibodies (e.g. those as mentioned above); or for the rapid evaluation of the safety of vaccines (e.g. influenza vaccines) and therapeutic antibodies. Other embodiments besides the above may be articulated as well. Numerous other objects, features and advantages of the present disclosure will become readily apparent from the detailed description.

Another aspect of the present invention is to disclose another experimental model which is developed by injecting anti-influenza immune sera or other anti-pathogen antibodies to pregnant mice and observing the healthy status of the pregnant dames and newborn mouse pups as described in exemplification. As described in exemplification, injection of the human anti-influenza viral sera into pregnant mice at pregnant day 16 (E16) and E19 induced abortion of the pregnant mice, immature or delayed delivery, and fatal and neonatal death of the newborn mouse pups delivered to the dames. The frequencies of fatal and neonatal death of the newborn mouse pups are listed in Table 3. The results with this animal model indicated that the antibodies induced by the H5N1 (avian) virus is at the highest risk for inducing death (34.6%), followed by the antibodies induced by the seasonal H1N1 virus (26.7%), and the H3N2 virus (26.5%), B influenza virus (23.5%), and the 2009H1N1 (swine) virus (22.9%). The frequencies of abortion of the pregnant mice are listed in Table 4. The results with this animal model indicated that the antibodies induced by the B influenza virus is at the highest risk for inducing abortion (33.3%), followed by the antibodies induced by the 2009H1N1 (swine) virus (31.3%), the H3N2 virus (28.6%), the seasonal H1N1 virus (21.4%), and the H5N1 (avian) virus (20.0%). The histology changes of the dead mice showed that the infiltration with red blood cells, inflammatory cells and proliferation of epithelium cells, and local tissue lesions were observed in the tissues of lung, brain, heart and liver of the dead chicks and mouse pups. In addition, binding of human IgG to those organs was detectable with the tissue sections of the dead chicks and mouse pups.

Taken together, the data with the animal models mentioned above strongly indicated that influenza infections or influenza vaccinations of pregnant females may be harmful to the fetus and newborns because some of the antibodies inducible by influenza vaccines may induce abortion, immature or delayed delivery and fetal and neonatal deaths. Further, some antibodies inducible by influenza viruses or influenza vaccines may cause autoimmune diseases or serious adverse reactions such as GBS or GBS-like condition and deaths. Similarly, some antibodies inducible by other pathogens or other vaccines may also cause autoimmune diseases or serious adverse reactions.

The experimental models can be used but not limited for the pathogenic study of infectious diseases, autoimmune diseases, infection-relating fetal and neonatal deaths, adverse reactions of influenza vaccines and other vaccines or therapeutic antibodies; for screening drugs for prevention and treatment of the disorders or conditions caused by harmful antibodies (e.g. those as mentioned above); or for the rapid evaluation of the safety of vaccines (e.g. influenza vaccines) and therapeutic antibodies. Other embodiments besides the above may be articulated as well. Numerous other objects, features and advantages of the present disclosure will become readily apparent from the detailed description of the experimental models.

New Pathogenic Mechanisms of Infections and Infection-Relating Disorders or Conditions One embodiment of the present invention discloses the new pathogenic mechanisms of infection-relation disorders or conditions including but not limited to infectious diseases, autoimmune diseases, cancer and other disorders possibly relating to infections.

One aspect of the present invention is to disclose a new concept of the pathogenic mechanisms of an infection. The mechanisms include but not limited to: 1) The initial, primary damage of cells, tissues or organs caused by viruses within week one; 2) The secondary damage is caused by anti-viral antibodies which are elevated from week one and reach peak levels from week two to week three after viral clearance; 3) the secondary damage can add further damage to the primary damage and cause sever disorders even death (primary plus secondary damages). 4) The secondary damage can be longer and broader because antibodies persist much longer than viruses. The primary plus secondary damages as mentioned above can cause serious conditions during an acute infection; and the persist antibodies can cause or make worse of the disordors or conditions such as autoimmune diseases, allergies, cancers and other disorders possibly relating to toxic antibodies.

Based on the pathogenic mechanisms mentioned above, antibodies against the viral strains of the 1918 and the 2009 influenza pandemic can be the major death cause of those influenza pandemics. This is supported by following evidences: 1) about ⅔ of deaths caused by the influenza infections occurred between week 2 to week 3 (Edwin O. Jordan. Epidemic Influenza—A survey, 1927) which was consistent to the time period of the antibody pick levels; and 2) the majority of severe or lethal infections happened to the youth (Edwin O. Jordan. Epidemic Influenza—A survey, 1927; WHO: Pandemic (H1N1) 2009-update 41) because younger people could induce higher levels of antibodies.

Another aspect of the present invention is to disclose a new pathogenic mechanism and the cause of autoimmune diseases. Besed on the above observations, some of the antibodies inducible by a pathogen or by a vaccine can bind to self cells or tissues or organs and mislead the immune response to attack the self. One example is that antibodies inducible by influenza viruses or influenza vaccines could cause GBS or fetal and neonatal deaths as described above. Another example is that injection of high dose of the anti-rotavirus antibodies to pregnant mice induced deaths and bile duct obstruction (biliary atresia) due to epithelium proliferation (inflammation) of mouse pups born to the dames (PCT/US2009/039810, US20110085981).

Another aspect of the present invention is to disclose a new pathogenic mechanism of cancers or other disorders (known or unknown). Many other disease processes such as cancers, diabetes, heart disease, and other disorders (known or unknown) arise from uncontrolled cell growth or defects in signal transduction pathways. Some of the antibodies induced during an infection or a vaccination or a therapeutic antibody can bind to certain cell-surface molecules and induce cellular proliferation or defects in signal transduction pathways. Repeatedly or persistent stimulation with such harmful antibodies can lead to uncontrolled cellular proliferation or defects in signal transduction pathways that lead to the development and progression of many types of cancers, autoimmune diseases, or other disorders (known or unknown). For example, anti-HIV antibodies stimulated proliferations of human lung cancer cells (A549) and liver cancer cells (HepG-2). Leukemia or lymphomas can be caused by some harmful antibodies inducible during an acute or a chronic infection (e.g. a human T-cell leukemia virus infection). The harmful antibodies can bind to the white blood cells including lymphocytes and stimulate the uncontrolled cellular proliferation of those blood cells, leading to leukemia or lymphomas.

Other embodiments besides the above may be articulated as well. Numerous other objects, features and advantages of the present disclosure will become readily apparent from the new disease causes (harmful antibodies) and the new pathogenic mechanisms.

Diseases and Conditions Inducible by Harmful Antibodies

In the present disclosure, the harmful antibodies can be induced during an infection (e.g. an influenza infection) or a vaccination (e.g. an influenza vaccination), or passively introduced (e.g. a therapeutic antibody). The diseases or conditions caused by harmful antibodies of the present disclosure include but not limited to infectious diseases, serious adverse reactions of vaccines or therapeutic antibodies, infection-relating autoimmune diseases, allergies, and inflammation, and infection-relating tumors, and other disorders (known or unknown).

The term “infectious diseases” refers to the invasion of a host organism's bodily tissues by disease-causing organisms, their multiplication, and the reaction of host tissues to these organisms and the toxins they produce. A short-term infection is an acute infection. A long-term infection is a chronic infection. Pathogens specific to infectious diseases suitable for use in this process include, but are not limited to viruses, bacteria, parasites, fungi, viroids, prions, protozoa, and insects, etc. Types of pathogens include but not limited to any types of pathogens, live or dead or inactivated, fresh or dried, fixed or frozen, whole or part or fragment, sections, smears, homogenates, lysates, and extracts of pathogens, and etc., without limitation. Examples of infections include but not limited to the disorders caused by influenza viruses, reoviruses, rotaviruses, cytomegaloviruses (CMV), Epstein-Barr viruses (EBV), adenoviruses, hepatitis viruses including HAV, HBV, HCV, human immunodeficiency virus (HIV), human T-cell leukemia viruses (HTLV), human papilloma viruses (HPV), polio viruses, parainfluenza viruses, measles viruses, mumps viruses, respiratory syncytial viruses (RSV), human herpes viruses (HHV), herpes simplex virus (HSV), Varicella-Zoster Virus, cholera viruses, pox virus, rabies virus, distemper virus, foot and mouth disease viruses, rhinoviruses, Newcastle disease viruses, pseudorabies virus, cholera, syphilis, anthrax, leprosy and bubonic plague, rickettsias, *neisseria gonorrhoeae, bordetella pertussis, escherichia coli, salmonella enterica, vibrio cholerae, pseudomonas aeruginosa, yersinia pestis, francisella tularensis, haemophilus influenzae*, purple sulfur bacteria, *helicobacter pylori, campylobacter jejuni, bacillus anthracis/cereus/thuringiensis, clostridium tetani, clostridium botulinum*, staphylococci, streptococci, pneumococci, *streptococcus pneumoniae*, mycoplasmas, *bacteroides fragilis, mycobacterium tuberculosis, mycobacterium leprae, corynebacterium diphtheriae, treponema pallidum, borrelia burgdorferi, chlamydia trachomatis, chlamydia psittaci*, phycocyanin, phycoerythrin, mitochondria, chloroplasts, etc without limitation.

According to the present invention, the term “infection-relating autoimmune diseases, allergies and inflammation” refers to the disorders or conditions caused by harmful antibodies induced during an infection or a vaccination or an antibody therapy. The disorders or conditions usually arise after a period time (e.g. within 4-8 weeks) of an infection or a vaccination. Examples of infection-relating autoimmune diseases, allergies and inflammation include but not limited to Guillain-Barre syndrome, autism, Kawasaki's disease, biliary atresia, primary biliary cirrhosis, systemic lupus erythematous, leukemia, acute leukemia, rheumatoid arthritis, adult onset diabetes mellitus (Type II diabetes), Sjogren's syndrome, juvenile onset diabetes mellitus, Hodgkin's and non-Hodgkin's lymphoma, malignant melanoma, cryoglobulinemia, hepatitis B virus infection, hepatitis C virus infection, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, dermatitis herpetiformis, alopecia areata, autoimmune cystitis, pemphigoid, scieroderma, progressive systemic sclerosis, CREST syndrome (calcinosis, Raynaud's esophageal dysmotility, sclerodactyly, and telangiectasia), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, pemphigus vulgaris, pemphigus, bullous pemphigoid, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, polymyalgia rheumatica, temporal arteritis, schistosomiasis, giant cell arteritis, ascariasis, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, renal cell carcinoma, multiple myeloma, Eaton-Lambert syndrome, relapsing polychondritis, Waldenstrom's macroglobulinemia, mumps virus infection, thrombotic throbocytopenic purpura, and any other disorder or conditions in which the specific recognition of the host by pathogen-inducible or vaccine-inducible antibodies is suspected or shown to be important in any aspect of the pathogenesis of the clinical illness. According to the present invention, the term "serious adverse reactions of vaccines or therapeutic antibodies" refers to the severe disorders or conditions caused by harmful antibodies induced during a vaccination or an antibody therapy. The disorders or conditions usually arise after a period time (e.g. within 4-8 weeks) of a vaccination or an antibody therapy. Examples of serious adverse reactions of vaccines of the present disclosure include but not limited to deaths, acute infant death syndrome, Guillain-Barre syndrome, Kawasaki's disease, acute leukemia, allergies, serious allergic reactions, asthma, epilepsy, immune system disorders, behavior disorders, nervous system injury, permanent brain damage, learning difficulties, seizure, severe seizures, lowered consciousness, autism, long-term coma, headaches, upper or low respiratory tract infection, joint pain, abdominal pain, cough, nausea, diarrhea, high fever, blood in the urine or stool, pneumonia, inflammation of the stomach or intestines, non-stop crying, fainting, deafness, temporary low platelet count, hives, pain in the joints, intussusception, vomiting, severe nervous system reaction, life-threatening severe illness with organ failure, still birth, neonatal deaths, and any other disorder or conditions in which the specific recognition of the host by vaccine-inducible antibodies is suspected or shown to be important in any aspect of the pathogenesis of the clinical illness.

According to the present invention, the term "infection-relating tumors" refers to the disorders or conditions with uncontrolled cell growth caused by harmful antibodies induced during an acute infection, or a vaccination or an antibody therapy, or a chronic infection, The disorders or conditions usually arise after a period time of an acute infection or a vaccination or an antibody therapy (e.g. acute leukemia). In addition, many tumors are developed by repeated stimulation of antibodies induced during a chronic infection. Examples of infection-relating tumors or cancers of the present disclosure include but not limited to acute or chronic leukemia, Hodgkin's and non-Hodgkin's lymphoma, malignant melanoma, tumors or cancers developed during infections of HIV, HTLV, HBV, HCV, EBV, CMV, HPV, HHV, HSV, adenoviruses, measles viruses, mumps viruses, varicella-zoster virus, lung cancers, liver cancer, prostate cancer, breast cancer, colon cancers, gastrointestinal cancers, pancreas cancers, cervical cancers, overall cancers, thyroid cancers, neurological cancers or tumors, renal cell carcinoma, kidney cancers, multiple myeloma, hemangioma, heart fibroid, and any other disorder or conditions in which the specific recognition of the host by pathogen-inducible or vaccine-inducible antibodies is suspected or shown to be important in any aspect of the pathogenesis of the clinical illness.

Therapeutic Products for Disorders or Conditions Inducible by Harmful Antibodies Based on the new causes and the new pathogenic mechanisms of the disorders or conditions inducible by harmful antibodies as mentioned above, one embodiment of the present invention discloses substances or products (new or existing) and approaches and the methods of uses of the substances or products (new or existing) and approaches for preventing and treating the disorders or conditions inducible by harmful antibodies by interrupting the binding of the harmful antibodies to host cells, tissues and organs, or by neutralizing the harmful antibodies. The products of the present disclosure include but not limited to serum or plasma, immunoglobulin, non-harmful antibodies, pathogen-deriving products, host-deriving products, saccharides, and any other substances or products (new or existing) capable of competing or neutralizing harmful antibodies.

Immunoglobulin or Serum or Plasma for Disorders Caused by Harmful Antibodies

One embodiment of the present invention discloses immunoglobulin products or serum or plasma and the methods of using the immunoglobulin products or the serum or the plasma for preventing and treating diseases and conditions relating to harmful antibodies from an infection or a vaccination, or an antibody therapy. The immunoglobulin or immunoglobulin in serum or plasma can compete, dilute and interrupt the binding of harmful antibodies to host cells, or tissues or organs, and protect the damages from harmful antibodies.

One aspect of the present invention discloses immunoglobulin products or serum or plasma for preventing and treating diseases or conditions (e.g. fetal and neonatal death) caused by harmful antibodies.

Wherein, the amounts or concentrations of an immunoglobulin product are from about 0.001 gram (g) to about 100 g. The amounts of a serum or plasma are from about 0.1 ml to 1000 ml. Wherein the immunoglobulin product or the serum or the plasma are in a form of a solution, a lyophilized, an injectable, an infusion, or a form conjugated to a nano-particle, or other using forms well known to those of ordinary skill in the relevant arts.

Wherein, the immunoglobulin products or the serum or the plasma are used for preventing or treating the diseases or conditions caused by harmful antibodies of the present disclosure. The diseases or conditions include but not limited to infectious diseases, serious adverse reactions of vaccines or therapeutic antibodies, infection-relating autoimmune diseases, allergies, and inflammation, and infection-relating tumors, and other disorders (known or unknown) as mentioned above.

Another embodiment of the present invention discloses the methods of using immunoglobulin products or serum or plasma for preventing and treating the diseases or conditions caused by harmful antibodies of the present disclosure. The diseases or conditions include but not limited to infectious diseases, serious adverse reactions of vaccines or therapeutic antibodies, infection-relating autoimmune diseases, allergies, and inflammation, and infection-relating tumors, and other disorders (known or unknown) as mentioned above.

One aspect of the methods is consisted administrate immunoglobulin products or serum or plasma to a human or an animal individual at risk of suffering or developing harmful antibody-inducible diseases or conditions as mentioned above.

Another aspect of the methods is consisted of administrate immunoglobulin products or serum or plasma to the feeding mothers of animals or humans with their sucking babies at risk of suffering or developing harmful antibody-inducible diseases or conditions as mentioned above.

Wherein, the pharmaceutical compositions or the therapeutic products can be provided to a biological organism including the feeding mothers mentioned above by a variety of routes such as subcutaneous, topical with or without occlusion, oral, intramuscular, intravenous (both bolus and infusion), intraperitoneal, intracavity, or transdermal, inhalant, or other using forms well known to those of ordinary skill in the pharmaceutical arts.

For example, injection of human immunoglobulin or healthy human serum or plasma to mouse pups before or after an influenza viral infection with a highly pathogenic influenza viral strain reduced about 50% of the deaths of the mice with the infection (Table 7), as described in the exemplification.

Another aspect of the present invention discloses immunoglobulin products or serum or plasma and the methods of using the immunoglobulin products or the serum or the plasma to prevent and treat serious adverse reactions of vaccines through vaccine-inducible antibodies.

For example, injection of human immunoglobulin or human serum or human plasma to pregnant mice prevented fatal and neonatal deaths (Tables 5-6), abortion, immature or delayed delivery of the dames, caused by the antibodies induced by influenza vaccines as described in the exemplification.

Another aspect of the present invention discloses immunoglobulin products or serum or plasma and the methods of using the immunoglobulin products or the serum or the plasma to prevent and treat to prevent and treat fetal and neonatal deaths caused by infections or vaccines.

Another aspect of the present invention discloses the methods of using human immunoglobulin products to prevent and treat infection-relating autoimmune diseases, allergy and inflammation.

Another aspect of the present invention discloses the methods of using human immunoglobulin products or human serum to prevent and treat infection-relating inflammation.

For therapeutic use as mentioned above, the effective dosage amounts of a serum or a plasma are from about 0.1 ml/kg to 100 ml/kg; the effective dosage amounts of a human Ig products are from about 1 mg/kg to 100 mg/kg.

Numerous other features or characteristics of therapeutic targets can become readily apparent from the detailed description.

A Method of Making Better Human Immunoglobulin or Antibody Products

One embodiment of the present invention discloses methods of making better human immunoglobulin products by mixing an immunoglobulin product or a therapeutic antibody with certain amount of N-acetylneuraminic acid, or an analog of N-acetylneuraminic acid (e.g. N-acetylneuraminic acid methyl ester) or N-acetylneuraminic acid plus an analog of N-acetylneuraminic acid (e.g. N-acetylneuraminic acid methyl ester)

The effective amount or concentration of N-acetylneuraminic acid or an analog of N-acetylneuraminic acid (e.g. N-acetylneuraminic acid methyl ester) are from 0.01 mg/g or 0.01 mg/ml to 100 mg/g or 100 mg/g.

Methods of Combination Use of Sialic Acid and Human Immunoglobulin or Serum or Plasma Products One embodiment of the present invention discloses methods of using immunoglobulin or serum or plasma products at the time of administration by mixing an immunoglobulin product or a therapeutic antibody with certain amount of N-acetylneuraminic acid, or an analog of N-acetylneuraminic acid (e.g. N-acetylneuraminic acid methyl ester) or N-acetylneuraminic acid plus an analog of N-acetylneuraminic acid (e.g. N-acetylneuraminic acid methyl ester), and administrate the mixture to a subject.

For therapeutic use as mentioned above, the effective dosage amounts of a serum or a plasma are from about 0.1 ml/kg to 100 ml/kg; the effective dosage amounts of a human Ig products are from about 0.1 mg/kg to 100 mg/kg. The effective dosages of N-acetylneuraminic acid or an analog of N-acetylneuraminic acid (e.g. N-acetylneuraminic acid methyl ester) are from 0.1 mg/kg to 100 mg/kg.

A Method of Making Better Human Immunoglobulin or Antibody Products

One embodiment of the present invention discloses methods of making better human immunoglobulin products at time of manufacturing by mixing an immunoglobulin or a serum or a plasma product or a therapeutic antibody with certain amount of N-acetylneuraminic acid, or an analog of N-acetylneuraminic acid (e.g. N-acetylneuraminic acid methyl ester) or N-acetylneuraminic acid plus an analog of N-acetylneuraminic acid (e.g. N-acetylneuraminic acid methyl ester)

The effective amount or concentration of N-acetylneuraminic acid or an analog of N-acetylneuraminic acid (e.g. N-acetylneuraminic acid methyl ester) are from 0.01 mg/g or 0.01 mg/ml to 100 mg/g or 100 mg/g.

Methods of Using Pathogens or Vaccines for Disorders Inducible by Harmful Antibodies A vaccine or an inactivated pathogen can be used as a therapeutic drug for the treatment of a severe infection caused by antibodies induced during an infection. The possible action mechanism of the therapeutic vaccines or inactivated pathogens is neutralization of harmful antibodies.

Specific Antibodies for Infection-Relating Diseases or Conditions

One embodiment of the present invention discloses antibodies specific to a first pathogen to be used for preventing and treating an infection caused by a second pathogen. The present invention also discloses the methods of using the specific antibody products for preventing and treating diseases and conditions relating to an infection. An antibody product comprises at least one of an immunoglobulin molecule or an immunologically active portion of an immunoglobulin molecule.

One aspect of the present invention discloses antibodies specific to a first pathogen (e.g. HAV or HBV or RSV) to be used for preventing and treating diseases or conditions caused by a second pathogen (e.g. an influenza virus).

Wherein, the amounts or concentrations of an antibody specific to a first pathogen are from about 0.001 gram (g) to about 100 g. Wherein the antibodies are in a form of a solution, a lyophilized, an injectable, an infusion, or a form conjugated to a nano-particle, or other using forms well known to those of ordinary skill in the relevant arts.

Wherein, the antibodies specific to a first pathogen are used for preventing or treating the diseases or conditions caused by a second pathogen. The diseases or conditions include but not limited to infectious diseases, serious adverse reactions of vaccines or therapeutic antibodies, infection-relating autoimmune diseases, allergies, inflammation, infection-relating tumors, and other disorders (known or unknown) as mentioned above.

Another embodiment of the present invention discloses the methods of using an antibody specific to a first pathogen and treating the diseases or conditions caused by a second pathogen. The diseases or conditions include but not limited to infectious diseases, serious adverse reactions of vaccines or therapeutic antibodies, infection-relating autoimmune diseases, allergies, inflammation, infection-relating tumors, and other disorders (known or unknown) as mentioned above.

One aspect of the methods is consisted administrate an antibody specific to a first pathogen to a human or an animal individual at risk of suffering or developing diseases or conditions caused by a second pathogen.

Another aspect of the methods is consisted of administrate an antibody specific to a first pathogen to the feeding mothers of animals or humans with their sucking babies at risk of suffering or developing an diseases or conditions caused by a second pathogen.

Wherein, the pharmaceutical compositions or the therapeutic products can be provided to a biological organism including the feeding mothers mentioned above by a variety of routes such as subcutaneous, topical with or without occlusion, oral, intramuscular, intravenous (both bolus and infusion), intraperitoneal, intracavity, or transdermal, inhalant, or other using forms well known to those of ordinary skill in the pharmaceutical arts.

For example, injection of human anti-HAV or -HBV or -RSV or rotavirus antibody to mouse pups before or after an influenza viral infection with a highly pathogenic influenza viral strain reduced about 50% of the deaths of the mice with the infection (Table 8), as described in the exemplification. Other examples include but not limited to:
a. Anti-H1N1 viral antibodies for protecting infections of H1N1, H3N2 or H5N1 virus;
b. Anti-H3N2 viral antibodies for protecting infections of H1N1 and H3N2 virus;
c. Anti-H5N1 viral antibodies for protecting infections of H1N1, H3N2 and H5N1 virus;
d. Anti-respiratory syncytial viral antibodies for protecting infections of influenza viruses and respiratory syncytial virus;
e. Anti-hepatitis A viral antibodies for protecting infections of influenza viruses and hepatitis A virus;

f. Anti-adenovirus antibodies for protecting infections of influenza viral infections; or g. Anti-rotavirus antibodies for protecting infections of influenza virus Another aspect of the present invention discloses the methods of using an antibody specific to a first pathogen to prevent and treat infection-relating autoimmune diseases, allergy and inflammation caused by a second pathogen.

Another aspect of the present invention discloses the methods of using an antibody specific to a first pathogen to prevent and treat infection-relating inflammation caused by a second pathogen.

As described above and in exemplification (Table 5, 6, 7), low dose of following immune sera or antibodies can be used as therapeutics for antibody-prevention and antibody-therapy of influenza infections.

a. Anti-seasonal H1N1 virus antibodies for the prevention of the 2009H1N1 (swine), other H1N1 and H5N1 influenza virus infection;
b. Anti-2009H1N1 (Swine) virus antibodies for the prevention of the other H1N1 and H5N1 influenza virus infection; and
c. Anti-H5N1 virus antibodies for the prevention of a H1N1 influenza virus infection.

For therapeutic uses as mentioned above, the effective dosage amounts of an antibody specific to a first pathogen are from about 0.001 ml/kg to 100 ml/kg.

Numerous other features or characteristics of therapeutic targets can become readily apparent from the detailed description.

In Vivo Proof of a Novel Action Mechanism of Vaccination and Antibodies

One embodiment of the present invention discloses a new functional mechanism of vaccines and anti-pathogen antibodies. The antibodies induced by an infection or a vaccine or acquired through passive immunity bind to and block at least one binding site of a pathogen.

Another experimental model is developed by injecting an anti-first pathogen antibody to an animal followed by infecting the animal with a second infectious pathogen as described in exemplification. The experimental models can be used but not limited for the screening and identifying shared binding sites by different pathogens, screening and testing new vaccines which is made of a first pathogen and protect the infection caused by a second pathogen. For example, the vaccines of HAV, HBV, RSV, rotavirus can be used for the prevention of influenza infection as described in exemplification.

An experimental model is developed by injecting an anti-first pathogen antibody to an animal followed by infecting the animal with a second infectious pathogen as described in exemplification. For example, day 5 mouse pups were injected separately with antibodies against HAV, HBV, RSV, adenovirus and rotavirus, followed by being infected with the A/PR/8/34(H1N1) influenza virus next day. Compared to the mouse pups pre-treated with saline, the mouse pups pre-treated with antibodies against HAV, HBV, RSV, adenovirus and rotavirus were not or lightly infected with the influenza virus. All the antibodies did not react with the influenza virus thus it was impossible for those antibodies functioning by neutralization of the influenza virus. The only possible action mechanism of the antibodies against a different pathogen (e.g. HAV) was blocking a shared viral binding site with the influenza virus.

This experiment discovered not only a new mechanism of vaccines or pathogen inducible antibodies, but also a new kind of vaccines which is made of a first pathogen and induce the antibodies which protect the infection caused by a second pathogen; or a new kind of antibodies specific to a first pathogen which can protect the infection caused by a second pathogen. Numerous other features or characteristics of such new therapeutics and the uses thereof can become readily apparent from the detailed description.

The experimental models can be used but not limited for the screening and identifying shared binding sites by different pathogens, screening and testing new vaccines which is made of a first pathogen and induce antibodies capable of protecting the infection caused by a second pathogen. For example, the vaccines of HAV, HBV, RSV, rotavirus can be used for the prevention of influenza infection as described in exemplification.

New Vaccines for Infectious Disease

One embodiment of the present invention discloses vaccines comprising a first pathogen which induces antibodies capable of protecting an infection caused by a second pathogen. The present invention also discloses the methods of using the specific vaccine made of the first pathogen capable of inducing antibodies for preventing and treating diseases and conditions relating to an infection caused by a second pathogen.

One aspect of the present invention discloses the vaccines comprising a first pathogen (e.g. HAV or HBV or RSV) and induce antibodies capable of preventing and treating diseases or conditions caused by a second pathogen (e.g. an influenza virus).

Wherein, the vaccines comprising a first pathogen are used for preventing or treating the diseases or conditions caused by a second pathogen. The diseases or conditions include but not limited to infectious diseases, serious adverse reactions of vaccines or therapeutic antibodies, infection-relating autoimmune diseases, allergies, and inflammation, and infection-relating tumors, and other disorders (known or unknown) as mentioned above.

Another embodiment of the present invention discloses the methods of using an antibody specific to a first pathogen and treating the diseases or conditions caused by a second pathogen. The diseases or conditions include but not limited to infectious diseases, serious adverse reactions of vaccines or therapeutic antibodies, infection-relating autoimmune diseases, allergies, and inflammation, and infection-relating tumors, and other disorders (known or unknown) as mentioned above.

One aspect of the methods is consisted of administrating a vaccines comprising a first pathogen to a human or an animal individual at risk of suffering or developing diseases or conditions caused by a second pathogen.

Another aspect of the methods is consisted of administrating vaccines comprising a first pathogen to the feeding mothers of animals or humans with their sucking babies at risk of suffering or developing an diseases or conditions caused by a second pathogen.

Wherein, the pharmaceutical compositions or the vaccines can be provided to a biological organism including the feeding mothers mentioned above by a variety of routes such as oral, intramuscular, inhalant, or other using forms well known to those of ordinary skill in the pharmaceutical arts.

New Methods of Use with Influenza Vaccines

One embodiment of the present invention discloses methods of using influenza vaccines. As described in exemplification, the influenza vaccine-induced anti-2009H1N1 (swine) and anti-H5N1 immune sera (pre-treated with Neu5Ac) were effective for prevention and treatment of the A/PR/8/34(H1N1) virus infection in mouse pups (Tables 6-7). These results provide in vivo evidence that two different influenza viruses (e.g. 2009H1N1 and H5N1 virus) can share at least one binding site. Thus blocking the shared binding site by a antibody induced by either virus can prevent and treat not only the infection of the virus (e.g. a H5N1 virus) but also the infection of the other virus (e.g. a H1N1 virus).

Another embodiment of the present invention is disclosing the methods of using a vaccine comprising one viral strain (e.g. the 2009H1N1 swine virus) for preventing the infections of a different viral strain (e.g. A/PR8/34H1N1 virus or a H5N1 virus). One aspect of the present invention disclose following new vaccines based on the shared binding sites.

a. A vaccine comprising a H1N1 viral strain for the prevention of the infections of a different H1N1 virus or a H5N1 virus; and b. A vaccine comprising a H5N1 virus for the prevention of the a H1N1 influenza infection.

Other example of the vaccines include but not limited to:
a. A vaccine comprising a H1N1 influenza virus for protection of H3N2 or H5N1 viral infection;
b. A vaccine comprising a H3N2 influenza virus for protection of H1N1 viral infection;
c. A vaccine comprising a H5N1 influenza virus for protection of H1N1 or H3N2 viral infection;
d. A vaccine comprising a respiratory syncytial virus for protection of influenza viral infections;
e. A vaccine comprising a hepatitis A virus for protection of influenza viral infections;
f. A vaccine comprising a adenovirus for protection of influenza viral infections; or
g. A vaccine comprising a rotavirus for protection of influenza viral infections.

Another aspect of the present invention discloses the methods of using a vaccine comprising a first pathogen to prevent and treat infection-relating autoimmune diseases, allergy and inflammation caused by a second pathogen.

For therapeutic use as mentioned above, the effective dosage amounts of a vaccine comprising to a first pathogen are at a amount to induce low to moderate levels of antibodies. Numerous other features or characteristics of therapeutic targets can become readily apparent from the detailed description.

Another embodiment of the present invention discloses a vaccine or an inactivated pathogen which can be used as a therapeutic for the treatment of a severe infection caused by antibodies induced during an infection. Another aspect of the invention is to disclose the methods of administrate a therapeutic product comprising a vaccine or an inactivated pathogen to a patient to prevent or treat the disorders or conditions caused by the antibodies against the vaccine or the pathogen induced during an infection. The possible action mechanism of the therapeutic vaccines or inactivated pathogens is neutralization of harmful antibodies.

Methods of Combination Use of Sialic Acid and Other Therapeutic Products

One embodiment of the present invention discloses methods of the combination uses of N-acetylneuraminic acid with other therapeutic products such as but not limited to immunoglobulin or serum or plasma products or antibody products at the time of administration by mixing such a therapeutic product with certain amount of N-acetylneuraminic acid, or an analog of N-acetylneuraminic acid (e.g. N-acetylneuraminic acid methyl ester) or N-acetylneuraminic acid plus an analog of N-acetylneuraminic acid (e.g. N-acetylneuraminic acid methyl ester), and administrate the mixture to a subject.

As described in exemplification, and shown in Tables 6-8, the combination uses of N-acetylneuraminic acid with non-specific human serum, or non-specific human immunoglobulin, or specific anti-infuenza antibodies, or a specific antibody to a non-influenza virus are significantly effective for the prevention of the H1N1 influenza infection. The data indicated that N-acetylneuraminic acid significantly increased the anti-infection efficacy of the non-specific human serum, or the non-specific human immunoglobulin, or the specific anti-influenza viral antibodies or the specific antibodies to a pathogen different from an influenza pathogen, and decreased the toxicity of a specific harmful antibody (e.g. an anti-influenza viral antibody).

For example, the anti-2009H1N1 (Swine), anti-seasonal-H1N1, and anti-H5N1 viral immune sera pre-mixed with N-acetylneuraminic acid showed best efficacy and lowest toxicity for prevention and treatment of influenza infections caused by A/PR/8/34(H1N1) virus in newborn mice (Table 6 and 7) as described in exemplification.

Another example as described in exemplification (Table 5), injection with moderate or high dose of antibodies against 2009H1N1 (swine), seasonal H1N1, avian H5N1 and B influenza viruses into chicken embryo at day 16 and day 19 induced the leg disability of newborn chicks which is similar to the Guillain-Barre syndrome (GBS) in human. However, newborn chicks with injection of the same antibodies pre-mixed with N-acetylneuraminic acid (Neu5Ac) did not develop the GBS-like condition (Table 5).

Another example as described in exemplification (Tables 5-7), the newborn mouse pups delivered to the dames treated with injection of the immune sera containing moderate to high dose of antibodies against 2009H1N1 (swine), seasonal H1N1, avian H5N1 and B influenza virus at embryo day 16 and 19 were sick or died; the newborn pups with injection of the immune sera mixture with N-acetylneuraminic acid did not developed disorders.

For such therapeutic uses as mentioned above, the effective dosage amounts of a serum or a plasma are from about 0.1 ml/kg to 100 ml/kg; the effective dosage amounts of a human Ig products are from about 0.1 mg/kg to 100 mg/kg. The effective dosages of N-acetylneuraminic acid or an analog of N-acetylneuraminic acid (e.g. N-acetylneuraminic acid methyl ester) are from 0.1 mg/kg to 100 mg/kg.

The possible action mechanism of N-acetylneuraminic acid is targeting harmful antibodies, thus it is effective as a drug one week after a vaccination or a viral infection. Numerous other features or characteristics of therapeutic targets can become readily apparent from the detailed description.

EXEMPLIFICATION

1. Antibodies and Therapeutics
   1.1 Following Immune Sera Were Tested as Described Below.
   a. Human immune plasma from three individuals immunized with the influenza vaccine made of the 2009H1N1 influenza virus (swine) and another three individuals naturally infected with the 2009H1N1 influenza virus (swine) (National influenza Center of China CDC).
      Antibody titers: 1:128-1:1280 (all adjusted to 1:128).
   b. Human immune sera from five individuals with natural infection of the 2009H1N1 influenza virus (swine) (National influenza Center of China CDC).
      Antibody titers: 1:80-1:160 (all adjusted to 1:80).
   c. Human immune sera from five individuals naturally infected with seasonal H1N1 influenza viruses (Guangdong/Baoan/2006, Guangdong/Luohu/2008, Tianjin/2009) (National influenza Center of China CDC).
      Antibody titers: 1:64-1:520 (all adjusted to 1:128 if possible).
   d. Human immune sera from three individuals with natural infection of a H3N2 influenza virus (Brisbane/59/Xinjiang/2007) (National influenza Center of China CDC).
      Antibody titers: 1:1280 (all adjusted to 1:128).
   e. Human immune serum from three individuals natural infected with a H5N1 (avian) influenza virus (Anhui, 2005) (National influenza Center of China CDC).
      Antibody titers: 1:64-1:512 (all adjusted to 1:128 if possible).
   f. Human immune serum from three individuals natural infected with a B influenza virus (Florida/4/Yunnan/2007) (National influenza Center of China CDC).
   g. Human serum or plasma pool consisted of sera or plasma from ten healthy individuals without infection or vaccination of influenza viruses.
      Antibody titers to a seasonal H1N1 virus: 1:5.
   1.2 Following Products Were Tested as Described Below.
   a. Human serum or plasma pool is as described above.
   b. A commercially available purified human immunoglobulin (Ig) (10%).
   c. A formulations comprising N-acetylneuraminic acid (1 mg/ml).
   1.3 Following Serum Mixtures Were Prepared as Described Below.
   a. Each 100 microliter of the human anti-09H1N1 (swine), anti-H1N1 (seasonal) and anti-H5N1 (avian) sera were mixed with each 100 microliter of the human serum pool
   b. Each 100 microliter of the human anti-09H1N1 (swine), anti-H1N1 (seasonal) and anti-H5N1 (avian) sera were mixed with each 100 micrograms of the human Ig. Each 100 microliter of the human anti-09H1N1 (swine), anti-H1N1 (seasonal) and anti-H5N1 (avian) sera were mixed with each 100 microliter of the formula comprising N-acetylneuraminic acid as mentioned above.

2. Experimental Models for evaluating the safety of Vaccines and Antibodies
   2.1 An Animal Model of Chicken Embryos and Newborn Chicks
   Chicken embryos were treated via allantois injection of various human anti-influenza viral immune sera or other anti-pathogen antibodies at day 16 (E16) and 19 (E19) and the healthy status of the newborn chicks were observed. The chicks were born at about E21.
   Eight groups of chicken embryos were treated at day 16 (E16) and 19 (E19) via allantois injection of each 100 microliter of 1) saline alone (n=20); 2) the human serum pool as mentioned above (n=20); 3) human serum from a RSV infected subject (n=20); 4) the human anti-2009H1N1 (swine) sera (n=40); 5) the human anti-seasonal H1N1 serum (n=40); 6) the human anti-H3N2 sera (n=40); 7) the human anti-H5N1 (avian) serum (n=40); and 8) the human anti-B viral sera (n=40). The chicken embryos were kept culturing in a 35° C. incubator until the newborn chicks were born at about E21.
   Injection of the anti-2009H1N1 sera, the anti-seasonal H5N1 (avian) sera and the anti-B sera as described above induced the leg disability of newborn chicks which is similar to the Guillain-Barre syndrome (GBS) in humans. The frequencies of GBS-like condition induced by the anti-influenza virus antibodies are listed in Table 1. The results indicated that the antibodies induced by the 2009H1N1 (swine) virus or the vaccine comprising the 2009H1N1 (swine) virus is at highest risk for inducing GBS-like disorders, followed by antibodies induced by the avian H5N1 (avian) virus and the influenza B virus. However, with reduced dosages (50 microliter or less), none of the sera induced significant disorders with the chicks treated with the antibody injections. The data indicated that moderate or high dose of anti-H1N1 (swine), anti-H5N1 and anti-B antibodies can induce serious adverse reactions of chicken embryos and newborn chicks.

TABLE 1

The frequency of GBS-like condition of newborn chicks with antibody injection

| Human immune serum | n = | GBS (%) | Odds Ratio | 95% CI | P |
|---|---|---|---|---|---|
| Saline | 20 | 0 (0.00) | Infinity | Infinity | Infinity |
| Normal seral pool* | 20 | 0 (0.00) | Infinity | Infinity | Infinity |
| Anti-RSV | 20 | 0 (0.00) | Infinity | Infinity | Infinity |
| Anti-H1N1/09 (swine)** | 40 | 17 (42.5) | 28.8 | 3.60-231 | <.0001 |
| Anti-H1N1/seasonal | 40 | 7 (17.5) | 8.27 | 0.97-70.7 | 0.06 |
| Anti-H3N2 | 40 | 6 (15.0) | 6.88 | 0.79-60.1 | 0.11 |
| Anti-H5N1 | 40 | 11 (27.5) | 14.8 | 1.81-121 | 0.003 |
| Anti-B | 40 | 13 (32.5) | 18.8 | 2.32-152 | 0.0007 |

*Seral pool of ten healthy individuals without infection or vaccination of influenza viruses
**Sera from subjects with either natural infection or vaccination of the 2009H1N1 influenza virus
RSV = Respiratory Syncytial Viruses;
GBS = Guillain-Barre syndrome In addition, injection of human anti-influenza viral sera induced fetal and neonatal deaths of the chicken embryos or newborn chicks. The death rates are listed in Table 2. The results with this animal model indicated that the antibodies induced by the B influenza virus is at the highest risk for inducing fetal and neonatal deaths (65.0%), followed by the antibodies induced by the avian H5N1 virus (57.5%), 2009H1N1 (swine) virus (52.5%), the H3N2 virus (37.5%) and the seasonal H1N1 virus (15.0%). As a control, the anti-respiratory syncytial viruses (RSV) serum did not cause significant GBS-like conditions nor deaths (Tables 1-2).

TABLE 2

The death frequecies of newborn chicks with antibody injection

| Human immune serum | n = | Death* (%) | Odds Ratio | 95% CI | P* |
|---|---|---|---|---|---|
| Normal seral pool | 40 | 3 (7.50) | 1.54 | 0.15-15.8 | 1.00 |
| Anti-RSV | 20 | 1 (5.00) | 0.65 | 0.06-6.67 | 1.00 |
| Anti-H1N1/09 (swine) | 40 | 21 (52.5) | 13.6 | 3.60-51.6 | <.0001 |
| Anti-H1N1/seasonal | 40 | 12 (30.0) | 5.29 | 1.36-20.5 | 0.02 |
| Anti-H3N2 | 40 | 15 (37.5) | 7.40 | 1.94-28.2 | 0.002 |
| Anti-H5N1 | 40 | 23 (57.5) | 14.7 | 4.40-63.3 | <.0001 |
| Anti-B serum | 40 | 26 (65.0) | 22.9 | 5.97-87.8 | <.0001 |
| Anti-H1N109 + Neu5Ac | 20 | 3 (15.0) | 0.16 | 0.04-0.63 | 0.01 |
| Anti-H1N1 + Neu5Ac | 20 | 1 (5.00) | 0.12 | 0.02-1.02 | 0.04 |
| Anti-H5N1 + Neu5Ac | 20 | 2 (10.0) | 0.08 | 0.02-0.41 | 0.0006 |

*Including fetal and neonatal death

In another experiment, the serum mixtures as prepared above in 1.3 were also tested using the animal model. Compared to injections of each anti-influenza viral serum alone, injection of the serum mixtures as mentioned above significantly reduced the GBS-like conditions or deaths (Tables 2) of the newborn chicks. A formula comprising N-acetylneuraminic acid methyl ester as an analog of N-acetylneuraminic acid was also tested with the method using N-acetylneuraminic acid as mentioned above. The results were similar to the results of N-acetylneuraminic acid as shown in Table 2.

The effective dosages of N-acetylneuraminic acid or an analog of N-acetylneuraminic acid (e.g. N-acetylneuraminic acid methyl ester) are from 0.1 mg/kg to 100 mg/kg.

2.2 An Animal Model of Pregnant Mice

Pregnant mice were treated twice via intraperitoneally (IP) injection of various human anti-influenza viral immune sera or other anti-pathogen antibodies at pregnancy day E16 and E19 respectively. The mouse pups were born at about E21 and the healthy status of the newborn mouse pups were observed.

As shown in Table 3-4, injection of the human anti-influenza viral sera into pregnant mice at pregnant day 16 (E16) and E19 induced abortion of the pregnant mice, immature or delayed delivery, and fatal and neonatal death of the newborn mouse pups delivered to the dames. The frequencies of fatal and neonatal death of the newborn mouse pups are listed in Table 3. The results with this animal model indicated that the antibodies induced by the H5N1 (avian) virus is at the highest risk for inducing death (34.6%), followed by the antibodies induced by the seasonal H1N1 virus (26.7%), and the H3N2 virus (26.5%), B influenza virus (23.5%), and the 2009H1N1 (swine) virus (22.9%).

TABLE 3

The death rates of mouse fetus or newborns with anti-influenza serum injection

| Human Serum | N = | Deaths | Rate(%) | Odds Ratio | 95% CI | P value |
|---|---|---|---|---|---|---|
| Normal seral pool | 53 | 3 | 5.66 | 1.03 | 0.10-10.7 | 1.00 |
| Anti-RSV | 18 | 1 | 6.70 | 0.79 | 0.08-8.22 | 1.00 |
| Anti-09H1N1 (swine) | 83 | 19 | 22.9 | 4.95 | 1.39-17.7 | 0.008 |
| Anti-H1N1 (seasonal) | 75 | 20 | 26.7 | 6.06 | 1.69-21.6 | 0.002 |
| Anti-H3N2 | 68 | 18 | 26.5 | 6.00 | 1.66-21.7 | 0.003 |
| Anti-H5N1 | 133 | 46 | 34.6 | 8.81 | 2.61-29.8 | <.0001 |
| Anti-B | 85 | 20 | 23.5 | 5.13 | 1.44-18.2 | 0.009 |

The frequencies of abortion of the pregnant mice are listed in Table 4. The results with this animal model indicated that the antibodies induced by the B influenza virus is at the highest risk for inducing abortion (33.3%), followed by the antibodies induced by the 2009H1N1 (swine) virus (31.3%), the H3N2 virus (28.6%), the seasonal H1N1 virus (21.4%), and the H5N1 (avian) virus (20.0%).

TABLE 4

The abortion frequecies of pregnant mice with anti-influenza serum injection

| Human Serum | N = | Abortion | Rate (%) | Odds Ratio | 95% CI | P |
|---|---|---|---|---|---|---|
| Normal seral pool* | 15 | 1 | 6.67 | 0.48 | 0.04-5.40 | 0.60 |
| Anti-09H1N1 (swine) | 16 | 5 | 31.3 | 6.36 | 0.65-62.7 | 0.18 |
| Anti-H1N1 (seasonal) | 14 | 3 | 21.4 | 3.82 | 0.35-42.0 | 0.33 |
| Anti-H3N2 | 14 | 4 | 28.6 | 7.78 | 0.78-77.9 | 0.08 |
| Anti-H5N1 | 20 | 4 | 20.0 | 3.50 | 0.35-35.1 | 0.36 |
| Anti-B | 15 | 5 | 33.3 | 7.00 | 0.71-69.5 | 0.17 |
| Anti-RSV | 3 | 0 | 0.00 | Infinity | Infinity | Infinity |

The histology changes of the dead mice showed that the infiltration with red blood cells, inflammatory cells and proliferation of epithelium cells, and local tissue lesions were observed in the tissues of lung (FIG. 1), brain, heart and liver of the dead chicks and mouse pups. In addition, binding of human IgG to those organs was detectable with the tissue sections of the dead chicks and mouse pups (data not shown).

Taken together, the present invention discloses a direct evidence for the first time that high levels of antibodies against influenza viruses are toxic to fetuses and newborns. According to our knowledge, this is the first direct proof of the association of influenza virus-inducible antibodies with the serious adverse reactions such as GBS-like condition and fetal or neonatal deaths. This finding suggests that vaccinating pregnant mothers with influenza vaccines may be risky for the fetuses and newborns.

3. Products for Prevention and Treatment of Disorder Caused by Harmful Antibodies 3.1 Therapeutics for Preventing and Treating Fetal and Neonatal Deaths The serum mixtures as prepared above in 1.3 were injected intraperitoneally twice to pregnant mice at pregnancy day E16 and E19 respectively. The mouse pups were born at about E21 and the healthy status of the newborn mouse pups were observed.

Compared to injections of each anti-influenza viral serum alone, injection of the serum mixtures as mentioned above to pregnant mice prevented fatal and neonatal deaths of those dames (Tables 5). In addition, no significant abortion, immature or delayed delivery of the dames treated with the serum mixtures were observed. A formula comprising N-acetylneuraminic acid methyl ester as an analog of N-acetylneuraminic acid was also tested with the method using N-acetylneuraminic acid as mentioned above. The results were similar to the results of N-acetylneuraminic acid as shown in Table 5.

TABLE 5

Therapeutics for preventing fetal and neonatal deaths caused by influenza antibodies

| Human Serum | N = | Deaths | Rate(%) | Odds Ratio | 95% CI | P value |
|---|---|---|---|---|---|---|
| Serum pool (SP) | 53 | 3 | 5.66 | 1.03 | 0.10-10.7 | 1.00 |
| Human Ig (H-Ig) | 20 | 1 | 5.00 | 0.88 | 0.09-8.96 | 1.00 |
| Anti-09H1N1 (swine) | 83 | 19 | 22.9 | 4.95 | 1.39-17.7 | 0.008 |
| Anti-09H1N1 + SP | 20 | 1 | 5.00 | 0.18 | 0.02-1.41 | 0.11 |
| Anti-09H1N1 + H-Ig | 22 | 1 | 4.55 | 0.16 | 0.02-1.27 | 0.06 |
| Anti-09H1N1 + Neu5Ac | 26 | 2 | 7.69 | 0.28 | .006-1.30 | 0.09 |
| Anti-H1N1 (S) | 75 | 20 | 26.7 | 6.06 | 1.69-21.6 | 0.002 |
| Anti-H1N1S + SP | 18 | 1 | 5.56 | 0.16 | 0.12-1.29 | 0.06 |
| Anti-H1N1S + H-Ig | 21 | 1 | 4.76 | 0.14 | 0.17-1.09 | 0.04 |
| Anti-H1N1S + Neu5Ac | 23 | 1 | 4.35 | 0.12 | 0.13-0.99 | 0.04 |
| Anti-H5N1 | 133 | 46 | 34.6 | 8.81 | 2.61-29.8 | <.0001 |
| Anti-H5N1 + SP | 21 | 2 | 9.52 | 0.20 | 0.04-0.89 | 0.02 |
| Anti-H5N1 + H-Ig | 23 | 2 | 8.70 | 0.18 | 0.04-0.80 | 0.01 |
| Anti-H5N1 + Neu5Ac | 28 | 3 | 10.7 | 0.23 | 0.07-0.79 | 0.01 |

Note:

SP = Serum Pool; Ig = Immunoglobulin: Neu5Ac = N-acetylneuraminic acid; S = Seasonal; H = Human.

Based on the data and observations, following products are effective for preventing or treating the disorders or conditions (e.g. GBS-like condition, fetal or neonatal death) caused by harmful antibodies: 1) the non-specific sera of healthy individuals; 2) human immunoglobulin; and 3) N-acetylneuraminic acid or an analog of N-acetylneuraminic acid (e.g. N-acetylneuraminic acid methyl ester).

For preventing or treating the disorders or conditions (e.g. GBS-like condition, fetal or neonatal death) caused by harmful antibodies as mentioned above, the effective dosage amounts of a serum or a plasma are from about 0.1 ml/kg to 100 ml/kg; the effective dosage amounts of a human Ig products are from about 0.1 mg/kg to 100 mg/kg; the effective dosages of N-acetylneuraminic acid or an analog of N-acetylneuraminic acid (e.g. N-acetylneuraminic acid methyl ester) are from 0.1 mg/kg to 100 mg/kg.

3.2 Therapeutics for Treating Influenza Infection

Ten groups of newborn bulb/c pups were inoculated at day 5 (P5) via oral and nasal administration of 30 μl (microliter) of the A/PR/8/34(H1N1) influenza virus (titer: 1:512, diluted 100 times with saline); and were treated at day 6 (P6) via intraperitoneal injection with 100 microliter of saline containing 1) saline alone; 2) 100 microliter of the human serum pool; 3) 100 mirograms of the human Ig; 4) 30 microliter of the human anti-2009H1N1 (swine) serum; 5) 30 microliter of the human anti-H1N1 serum: 6) 30 microliter of the human anti-H5N1 serum; 7) a mixture of 30 microliter of the human anti-2009H1N1 (swine) serum plus 100 micrograms of N-acetylneuraminic acid (Neu5Ac); 8) a mixture of 30 microliter of the human anti-H5N1 serum plus 100 micrograms of Neu5Ac; 9) a mixture of 100 microliter of the human serum pool plus 100 micrograms of Neu5Ac; and 10) 100 micrograms of the human Ig plus 100 micrograms of Neu5Ac. Mice were kept for 7 days after infection.

TABLE 6

Therapeutics for treating influenza infection of A/PR/8/34(H1N1) virus

| Human Serum | n = | Death | Death (%) | Odds Ratio | 95% CI | P |
|---|---|---|---|---|---|---|
| Saline | 20 | 17 | 87.0 | 6.67 | 1.53-29.1 | 0.02 |
| Serum pool (10) | 22 | 11 | 50.0 | 0.17 | 0.04-0.78 | 0.02 |
| Human Ig | 21 | 9 | 42.9 | 0.13 | 0.01-0.41 | 0.001 |
| Anti-09H1N1 (swine) | 13 | 13 | 100 | Infinity | Infinity | Infinity |
| Anti-H1N1 (seasonal) | 15 | 15 | 100 | Infinity | Infinity | Infinity |
| Anti-H5N1(avian) | 13 | 6 | 46.2 | 0.15 | .03-0.78 | 0.03 |
| Anti-09H1N1 + Neu5Ac | 22 | 4 | 18.2 | 0.04 | .008-0.20 | <.0001 |
| Anti-H5N1 + Neu5Ac | 21 | 4 | 19.1 | 0.04 | .008-0.21 | <.0001 |
| Serum pool + Neu5Ac | 21 | 6 | 28.6 | 0.07 | 0.02-0.33 | 0.0009 |
| Human Ig + Neu5Ac | 20 | 5 | 25.0 | 0.06 | 0.01-0.29 | 0.0003 |

Note:
Ig = Immunoglobulin; Neu5Ac = N-acetylneuraminic acid: S = Seasonal.

As summarized in Table 6, 17/20 (87%) of the pups treated with saline, and all (100%) of the pups treated with the anti-2009H1N1 serum alone or the anti-seasonal H1N1 serum alone died at day 3 after viral infection. 50% or more of the pups treated with the human serum pool (50%) or the human Ig (57.1%) or the anti-H5N1 serum survived. The death rates of the pups treated with the serum mixtures with N-acetylneuraminic acid were significantly reduced (Table 6). The results indicated that N-acetylneuraminic acid can significantly reduce the toxicity of the harmful antibodies or increase the efficacy of the human Ig or human serum or plasma for the treatment of an serious influenza infection. The data also suggested that high dose of the anti-20009H1N1 (swine) antibodies alone are harmful rather than helpful for the treatment of an influenza infection.

For treating influenza infections, the effective dosage amounts of a serum or a plasma are from about 0.1 ml/kg to 100 ml/kg; the effective dosage amounts of a human Ig products are from about 0.1 mg/kg to 100 mg/kg; the effective dosages of N-acetylneuraminic acid or an analog of N-acetylneuraminic acid (e.g. N-acetylneuraminic acid methyl ester) are from 0.1 mg/kg to 100 mg/kg.

3.3 Therapeutics for Preventing Influenza Infection

In another experiment using the mouse model mentioned above in 3.2, ten groups of newborn bulb/c mouse pups were pretreated at day 5 (P5) via intraperitoneal injection with the sera and the serum mixtures as mentioned above in 3.2. The pups were inoculated at day 6 (P6) via oral administration of 30 μl (microliter) of the A/PR/8/34(H1N1) virus (titer: 1:512, diluted 100 times with saline), and kept for 7 days after viral infection.

The results are summarized in Table 7. The data indicated that 1) the human serum pool or the human immunoglobulin alone or the anti-H5N1 reduced the death rate of the A/PR/8/34(H1N1) infection from 87.0% to 50% or 42.9% (1.74-2.0 folds); 2) the specific anti-seasonal H1N1 serum or the anti-2009H1N1 (swine) serum (containing specific antibodies at a titer of 1:128) is not effective or harmful for the prevention of the A/PR/8/34(H1N1) infection; and 3) the combination uses of N-acetylneuraminic acid with non-specific human serum, or non-specific human immunoglobulin, or specific anti-influenza antibodies and N-acetylneuraminic acid are significantly effective for the prevention of the H1N1 influenza infection; and 4) N-acetylneuraminic acid significantly increased the anti-infection efficacy of non-specific human serum, or non-specific human immunoglobulin, or specific anti-influenza viral antibodies, and decreased the toxicity of a specific harmful antibody (e.g. an anti-influenza viral antibody).

TABLE 7

Therapeutics for preventing influenza infection of A/PR/8/34(H1N1) virus

| Human Serum | n = | Death | Death (%) | Odds Ratio | 95% CI | P |
|---|---|---|---|---|---|---|
| Saline | 21 | 18 | 85.7 | 6.00 | 1.30-27.8 | 0.04 |
| Serum pool (10) | 18 | 9 | 50.0 | 0.17 | 0.03-0.77 | 0.04 |
| Human Ig | 20 | 9 | 45.0 | 0.14 | 0.03-0.62 | 0.001 |
| Anti-09H1N1 (swine) | 12 | 12 | 100 | Infinity | Infinity | Infinity |
| Anti-H1N1 (seasonal) | 11 | 11 | 100 | Infinity | Infinity | Infinity |
| Anti-H5N1(avian) | 12 | 6 | 50.0 | 0.17 | .003-0.88 | 0.04 |
| Anti-09H1N1 + Neu5Ac | 23 | 4 | 17.4 | 0.04 | .007-0.18 | <.0001 |
| Anti-H5N1 + Neu5Ac | 21 | 3 | 14.3 | 0.03 | .005-0.16 | <.0001 |
| Serum pool + Neu5Ac | 20 | 6 | 30.0 | 0.07 | 0.02-0.34 | 0.0004 |
| Human Ig + Neu5Ac | 23 | 6 | 26.1 | 0.06 | 0.01-0.27 | <.0001 |

Note:
Ig = Immunoglobulin; Neu5Ac = N-acetylneuraminic acid; S = Seasonal.

For preventing influenza infections, the effective dosage amounts of a serum or a plasma are from about 0.1 ml/kg to 100 ml/kg; the effective dosage amounts of a human Ig products are from about 0.1 mg/kg to 100 mg/kg; the effective dosages of N-acetylneuraminic acid or an analog of N-acetylneuraminic acid (e.g. N-acetylneuraminic acid methyl ester) are from 0.1 mg/kg to 100 mg/kg.

3.4 Another Experimental Model

A mouse model is developed by injecting an anti-first pathogen antibody to an animal followed by infecting the animal with a second infectious pathogen.

Six groups of newborn bulb/c mouse pups were pretreated at day 5 (P5) via intraperitoneal injection with other antibodies to other pathogens, which did not react with an influenza virus as described below. The pups were inoculated at day 6 (P6) via oral administration of 30 µl (microliter) of the A/PR/8/34(H1N1) virus (titer: 1:512, diluted 100 times with saline), and kept for 7 days after viral infection. The tested antibodies to other pathogens were:

a. The human immune sera from subjects infected with RSV;
b. The human immune sera from subjects infected with HAV;
c. The human immune sera from subjects infected with HBV;
d. The human immune sera from subjects infected with rotavirus.

All the antibodies did not react with the influenza virus.

The results are summarized in Table 8. Compared to the mouse pups pre-treated with saline, the mouse pups pre-treated with antibodies against HAV, HBV, RSV, and rotavirus were not or lightly infected with the influenza virus. The data indicated that an antibody against a first pathogen (e.g. HAV) can prevent an infection of a second pathogen.

In addition, the combination uses of N-acetylneuraminic acid with those specific antibodies to a pathogen different from an influenza pathogen significantly increased the antibody efficacy for the prevention of the H1N1 influenza infection.

TABLE 8

Various antibodies for preventing influenza infection of A/PR/8/34(H1N1) virus

| Human Serum | n = | Death | Death (%) | Odds Ratio | 95% CI | P |
| --- | --- | --- | --- | --- | --- | --- |
| Saline | 20 | 18 | 90.0 | 9.00 | 1.60-50.7 | 0.01 |
| Serum pool (10) | 18 | 9 | 50.0 | 0.11 | 0.02-0.63 | 0.01 |
| Anti-H1N1(S) | 12 | 11 | 91.7 | 1.22 | 0.10-15.1 | 1.00 |
| Anti-RSV | 14 | 1 | 7.14 | 0.01 | .0007-0.10 | <.0001 |
| Anti-Rotavirus | 11 | 2 | 18.2 | 0.03 | .003-0.21 | <.0001 |
| Anti-HAV | 13 | 2 | 15.4 | 0.02 | .0003-0.16 | <.0001 |
| Anti-HBV | 12 | 3 | 25.0 | 0.04 | .005-0.26 | 0.0003 |

Note:
Neu5Ac = N-acetylneuraminic acid; S = Seasonal.

For preventing an influenza infections, the effective dosage amounts of the specific antibodies to a pathogen different from an influenza pathogen are from about 0.001 mg/kg to 100 mg/kg; the effective dosages of N-acetylneuraminic acid or an analog of N-acetylneuraminic acid (e.g. N-acetylneuraminic acid methyl ester) are from 0.1 mg/kg to 100 mg/kg.

3.4 Combination Use of Therapeutic Antibodies with N-Acetylneuraminic Acid

As mentioned above and shown in Tables 6-8, the combination uses of N-acetylneuraminic acid with non-specific human serum, or non-specific human immunoglobulin, or specific anti-infuenza antibodies, or a specific antibody to a non-influenza virus are significantly effective for the prevention of the H1N1 influenza infection. The data indicated that N-acetylneuraminic acid significantly increased the anti-infection efficacy of the non-specific human serum, or the non-specific human immunoglobulin, or the specific anti-influenza viral antibodies or the specific antibodies to a pathogen different from an influenza pathogen, and decreased the toxicity of a specific harmful antibody (e.g. an anti-influenza viral antibody).

Additional Definitions

As used herein, the term "treating" or "treatment" refers to clinical intervention (such as, e.g., administration of an immunoglobulin product, serum, or plasma, as described herein) designed to alter the natural course of the individual or cell being treated during the course of clinical pathology of a viral infection. Desirable effects of treatment include decreasing the rate of disease progression or mortality, ameliorating or palliating the disease state, and remission or improved prognosis. In some embodiments, the treatment improves symptoms of viral infection (e.g., an influenza viral infection), reduces frequency or severity of the disease caused by the viral infection (e.g., influenza), and/or improves patient-reported symptoms (e.g., such as symptoms of influenza, including, but not limited to, e.g., fever, chills, cough, sore throat, body aches, and fatigue). A response is achieved when the patient experiences partial or total alleviation, or reduction of signs or symptoms of illness, and, in some embodiments, includes survival. A subject is successfully "treated," for example, if one or more symptoms associated with a viral infection (such as influenza) are mitigated or eliminated.

As used herein, the term "preventing" or "prevention" includes providing prophylaxis with respect to occurrence or recurrence of viral infection (such as influenza) in an individual. An individual may be predisposed to or susceptible to viral infection (such as infection by an influenza virus), but has not yet been infected with the virus.

As used herein, an individual "at risk" of viral infection (such as influenza infection) denotes that an individual is likely to be exposed to a viral pathogen or has one or more risk factors of having severe reactions to viral pathogen if infected.

An "effective amount" refers to at least an amount of immunoglobulin product, serum or plasma, as described herein, that is effective, at dosages and for periods of time necessary, to achieve the desired or indicated effect, including a therapeutic or prophylactic result. An effective amount can be provided in one or more administrations.

As used herein, the term "patient" or "individual" refers to a mammal, including, but not limited to, a human or non-human mammal, such as a bovine, equine, porcine, canine, ovine, or feline. In some embodiments, the patient or individual is a human. In some embodiments, the patient is not in need of a blood transfusion due to, e.g., an injury or bleeding clotting disorder such as, but not limited to, e.g., hemophilia, von Willebrand disease, and leukemia.

In some embodiments, the patient and the healthy individual are both human. In some embodiments, the patient and the healthy individual are both cows, sheep, chickens, pigs, horses, dogs, or cats.

As used herein, the patient in the present invention comprises human or non-human mammal of males and females, newborns, 1-12 months old infants, 1-18 years old, adults, pregnant and feeding females, and pregnant or feeding females with their fetus or sucking babies at risk of suffering or developing the diseases and conditions caused by harmful antibodies.

BRIEF DESCRIPTION OF THE DRAWING

FIG. 1 is a graphical representation of histology changes of lungs from the mouse pups delivered to the dams treated with human serum of healthy individuals (A) or the anti-09H1N1 influenza virus serum (B). This data showed that antibodies induced by the 09H1N1 influenza virus are harmful to fetuses and newborns since it caused later fetal death (still birth) and neonatal death.

ADDITIONAL EMBODIMENTS

Another embodiment of the present invention discloses therapeutic products comprising a vaccine or an inactivated pathogen for the treatment of a severe infection caused by antibodies induced during an infection; wherein the therapeutic vaccines or inactivated pathogens neutralize harmful antibodies induced during the infection.

Another embodiment of the present invention discloses a method of administrating a therapeutic vaccine or an inactivated pathogen to a patient to prevent or treat the disorders or conditions caused by the antibodies against the vaccine or the pathogen; wherein the antibodies are induced during an infection; the therapeutic vaccines or inactivated pathogens neutralize harmful antibodies induced during the infection.

Other embodiments besides the above may be articulated as well. The terms and expressions therefore serve only to describe the disclosure by example only and not to limit the disclosure. It is expected that others will perceive differences, which while differing from the foregoing, do not depart from the spirit and scope of the disclosure herein described and claimed. All patents, patent publications, and other references cited herein are incorporated herein by reference in their entirety.

What claimed is:

1. A method of treating a patient infected by an influenza virus, the method comprising administering an effective amount of N-acetylneuraminic acid and an immunoglobulin product, serum, or plasma to the patient, wherein
   the immunoglobulin product, the serum, or the plasma is obtained from a healthy individual, and
   the effective amount comprises about 0.1 mg/kg to about 100 mg/kg of N-acetylneuraminic acid per kg body weight of the patient.

2. The method of claim 1, wherein the influenza virus is 2009 H1N1 (swine flu), B influenza, H5N1 (avian flu), H1N1, or H3N2.

3. The method of claim 1, wherein the effective amount of the immunoglobulin product is between about 0.001 grams to about 100 grams.

4. The method of claim 1, wherein the effective amount of the serum or the plasma is between about 0.1 ml to about 1000 ml.

5. The method of claim 1, wherein the immunoglobulin product, the serum, or the plasma is in the form of a solution, a lyophilized, an injectable, an infusion, or a form conjugated to a nanoparticle.

6. The method of claim 1, wherein the N-acetylneuraminic acid is present in the composition at a concentration of between about 0.01 mg/ml and about 100 mg/ml.

7. The method of claim 1, wherein the immunoglobulin product, the serum, or the plasma is administered subcutaneously, topically, orally, intramuscularly, intravenously, intraperitoneally, intracavitally, or transdermally, or via inhalation.

8. The method of claim 1, wherein the patient and the healthy individual are both mammals of the same species.

9. The methods of claim 8, wherein the patient and the healthy individual are both cows, sheep, chickens, pigs, horses, dogs, or cats.

10. The method of claim 8, wherein the patient and the healthy individual are both human.

11. The method of claim 1, wherein the method further comprises administering an analog of N-acetylneuraminic acid.

12. The method of claim 11, wherein the analog of N-acetylneuraminic acid comprises N-acetylneuraminic acid methyl ester.

13. The method of claim 1, wherein the method comprises administering an effective amount of the N-acetylneuraminic acid and an immunoglobulin product to the patient.

14. The method of claim 1, wherein the method comprises administering an effective amount of the N-acetylneuraminic acid and a serum to the patient.

15. The method of claim 1, wherein the method comprises administering an effective amount of the N-acetylneuraminic acid and a plasma to the patient.

\* \* \* \* \*